United States Patent
Kawagishi et al.

(10) Patent No.: US 9,907,533 B2
(45) Date of Patent: Mar. 6, 2018

(54) ULTRASONIC DIAGNOSIS APPARATUS AND DISPLAYING METHOD

(75) Inventors: Tetsuya Kawagishi, Nasushiobara (JP); Katsuhisa Ishii, Kobe (JP)

(73) Assignees: Toshiba Medical Systems Corporation, Otawara-shi (JP); THE KANSAI ELECTRIC POWER CO., INC., Osaka-shi (JP)

( * ) Notice: Subject to any disclaimer, the term of this patent is extended or adjusted under 35 U.S.C. 154(b) by 1381 days.

(21) Appl. No.: 12/791,531

(22) Filed: Jun. 1, 2010

(65) Prior Publication Data
US 2010/0305445 A1 Dec. 2, 2010

(30) Foreign Application Priority Data
Jun. 2, 2009 (JP) .................................. 2009-132799

(51) Int. Cl.
*A61B 8/00* (2006.01)
*A61B 8/08* (2006.01)
*G01S 7/52* (2006.01)

(52) U.S. Cl.
CPC ............ *A61B 8/0883* (2013.01); *A61B 8/481* (2013.01); *G01S 7/52071* (2013.01); *G01S 7/52073* (2013.01)

(58) Field of Classification Search
USPC ....... 600/407, 411, 437, 443, 447, 458, 463; 382/131, 164, 165
See application file for complete search history.

(56) References Cited

U.S. PATENT DOCUMENTS

| | | | | | |
|---|---|---|---|---|---|
| 4,896,364 | A | * | 1/1990 | Lohscheller | ................... 382/162 |
| 5,195,521 | A | * | 3/1993 | Melton et al. | ................. 600/438 |
| 5,243,987 | A | * | 9/1993 | Shiba | .............................. 600/463 |
| 5,253,644 | A | * | 10/1993 | Elmvist | ............................ 607/14 |
| 5,483,963 | A | * | 1/1996 | Butler et al. | ................... 600/437 |
| 5,743,266 | A | * | 4/1998 | Levene | .................... A61B 8/06 |
| | | | | | 600/458 |

(Continued)

FOREIGN PATENT DOCUMENTS

| | | |
|---|---|---|
| JP | 2007-143606 | 6/2007 |
| WO | WO 96/33655 | 10/1996 |
| WO | WO 2005/072617 A1 | 8/2005 |

OTHER PUBLICATIONS

Kunichika et al., "Visualization of Risk-Area Myocardium as a High-Intensity, Hyperenhanced "Hot Spot" by Myocardial Contrast Echocardiography Following Coronary Reperfusion." vol. 42, No. 3, 2003. pp. 552-557.*

(Continued)

*Primary Examiner* — James Kish
(74) *Attorney, Agent, or Firm* — Oblon, McClelland, Maier & Neustadt, L.L.P.

(57) ABSTRACT

According to one embodiment, an ultrasonic diagnosis apparatus includes a display unit to display an ultrasonic image, a comparison unit to compare the signal/echo intensity of a cardiac chamber portion of an ultrasonic image with the signal/echo intensity of a myocardial portion of the image, and an indication generating unit to generate a specific indication at a time point when the signal/echo intensity of the cardiac chamber portion changes from a higher value to a lower value than the signal/echo intensity of the myocardial portion or at another time point with reference to the time point.

19 Claims, 6 Drawing Sheets

(56) References Cited

U.S. PATENT DOCUMENTS

| | | | |
|---|---|---|---|
| 5,980,460 A * | 11/1999 | Østensen et al. | 600/454 |
| 6,015,384 A * | 1/2000 | Ramamurthy et al. | 600/440 |
| 6,222,948 B1 * | 4/2001 | Hossack et al. | 382/294 |
| 6,352,509 B1 | 3/2002 | Kawagishi et al. | |
| 2001/0056236 A1 | 12/2001 | Angelsen | |
| 2002/0087072 A1 * | 7/2002 | Breeuwer | G06T 7/606 600/420 |
| 2004/0138567 A1 * | 7/2004 | Ito et al. | 600/458 |
| 2006/0004279 A1 * | 1/2006 | Ikeda et al. | 600/411 |
| 2006/0155185 A1 * | 7/2006 | Breeuwer | A61B 5/055 600/407 |
| 2008/0077013 A1 * | 3/2008 | Kawagishi et al. | 600/443 |
| 2008/0119718 A1 * | 5/2008 | Hundley et al. | 600/407 |
| 2008/0146931 A1 * | 6/2008 | Zhang et al. | 600/447 |
| 2008/0317316 A1 * | 12/2008 | Ohuchi et al. | 382/131 |

OTHER PUBLICATIONS

Extended European Search Report dated Sep. 27, 2010, in Application No. 10005707.4-2319.

* cited by examiner

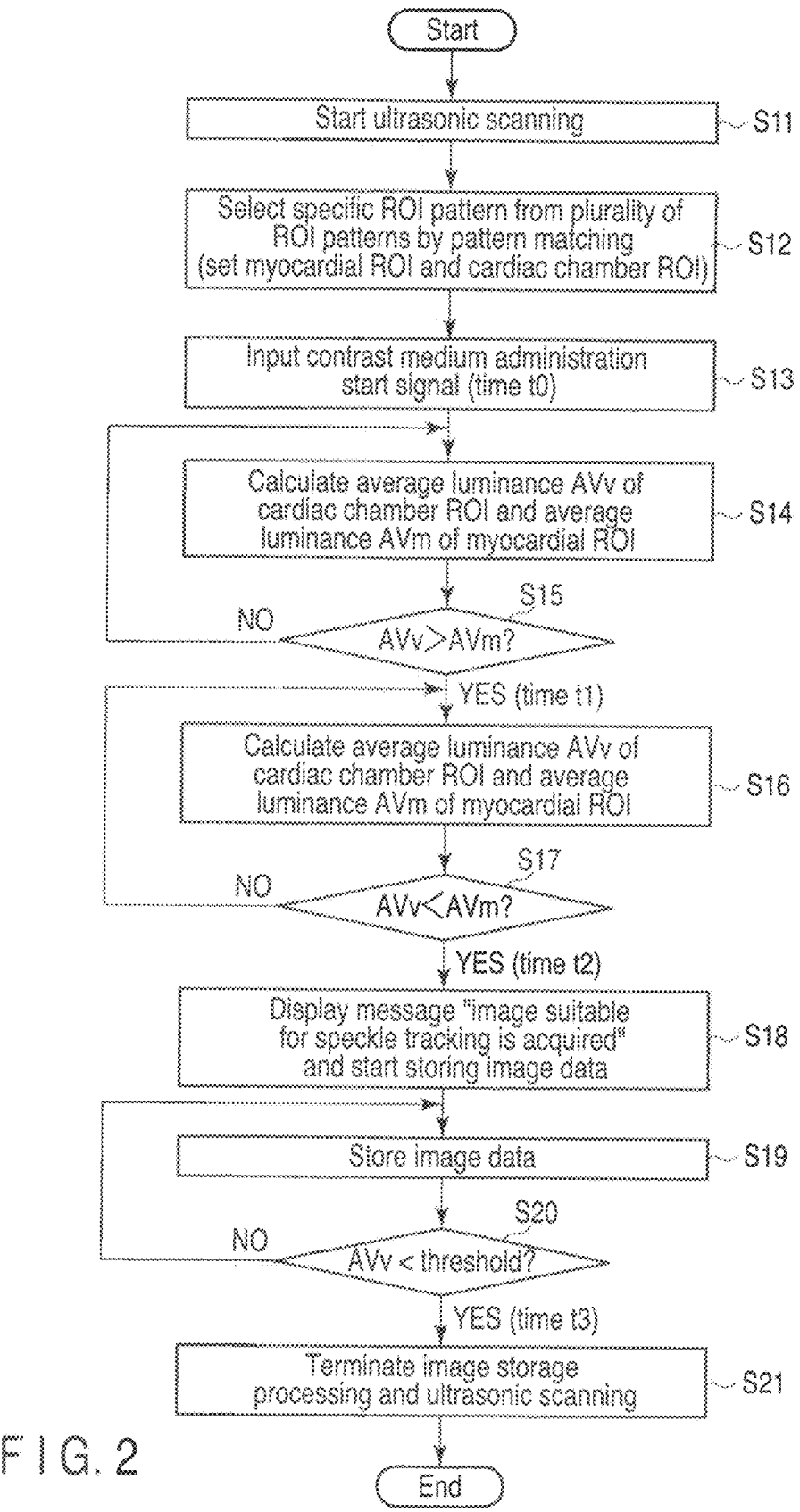
F I G. 2

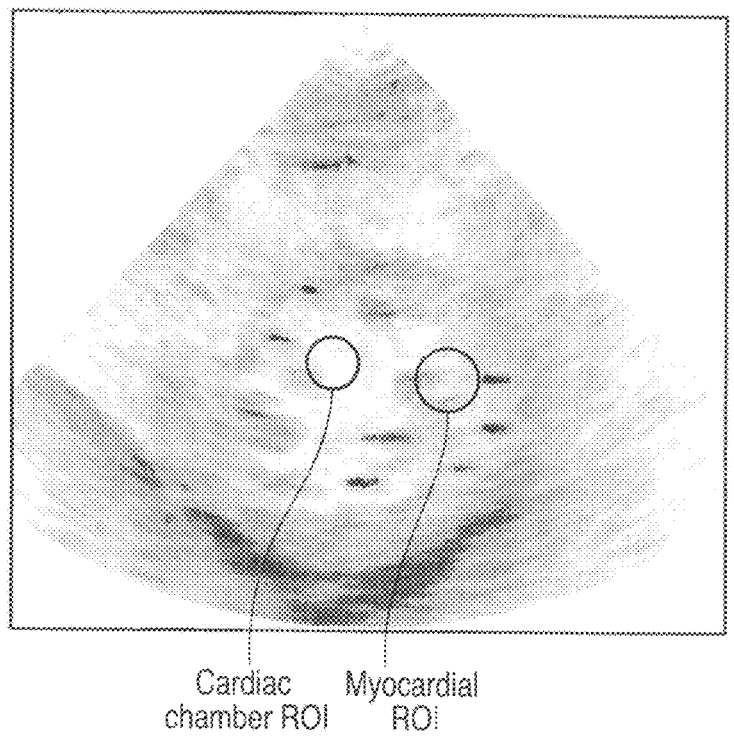
F I G. 4
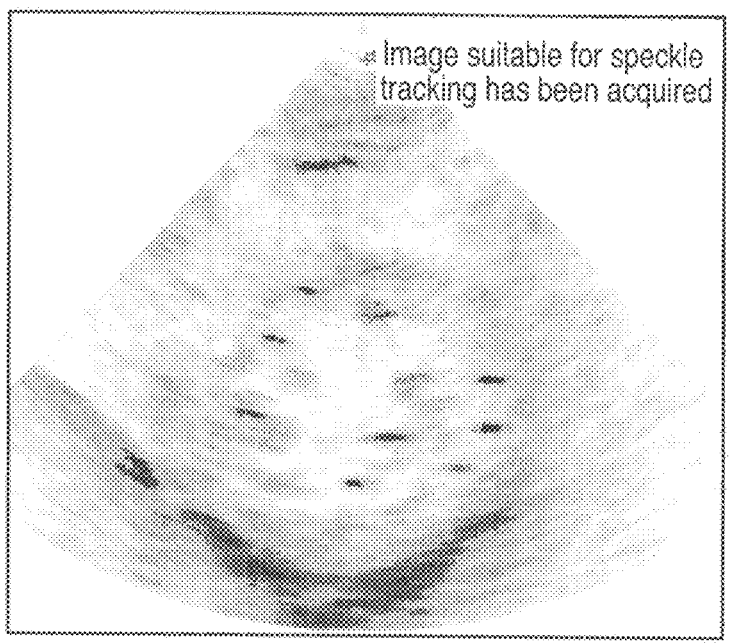
F I G. 5

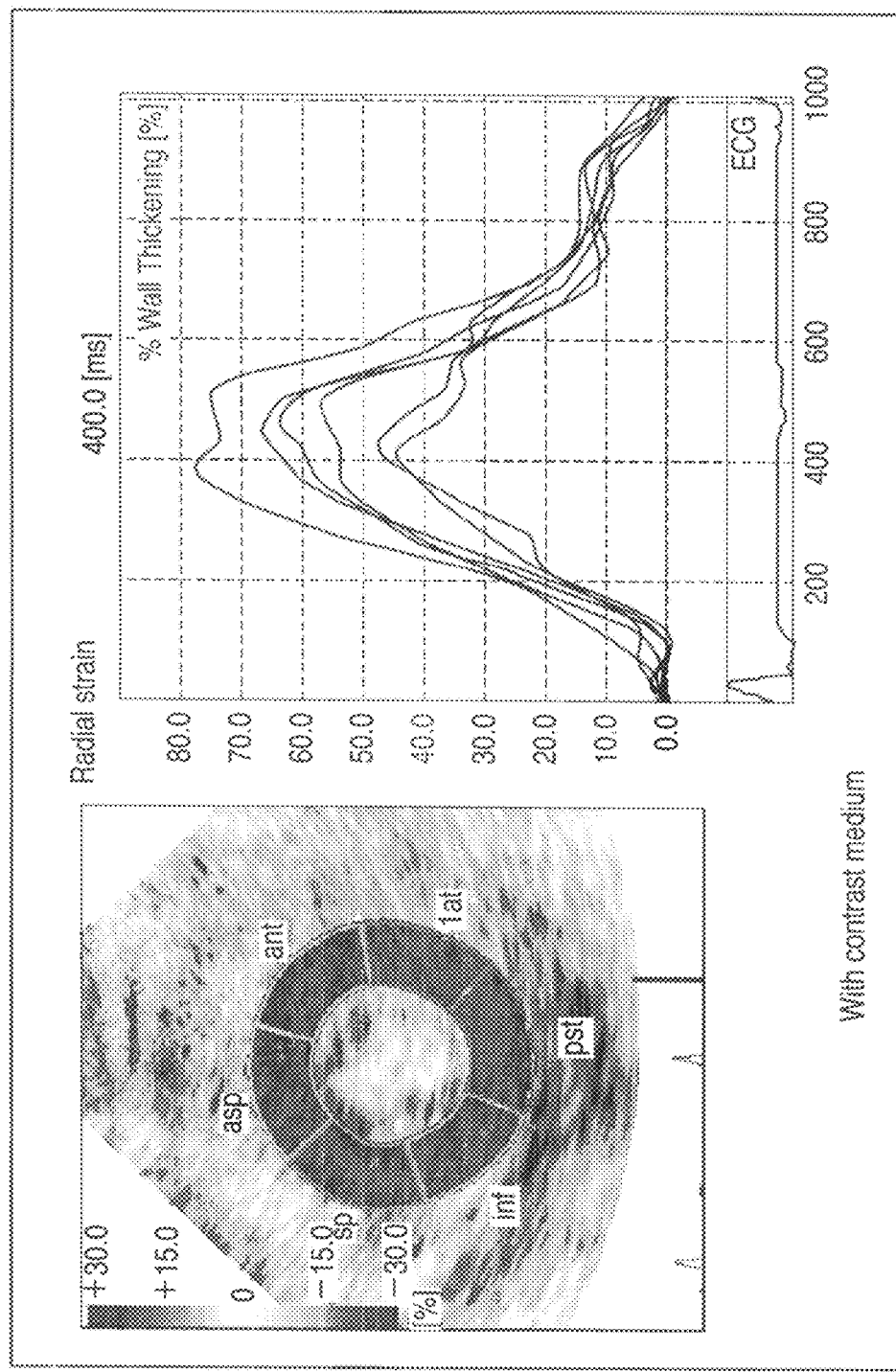
F I G. 7

ULTRASONIC DIAGNOSIS APPARATUS AND DISPLAYING METHOD

CROSS-REFERENCE TO RELATED APPLICATIONS

This application is based upon and claims the benefit of priority from Japanese Patent Application No. 2009-132799, filed Jun. 2, 2009; the entire contents of which are incorporated herein by reference.

FIELD

Embodiments described herein relate generally to an ultrasonic diagnosis apparatus and displaying method.

BACKGROUND

There have been growing needs for the quantitative evaluation of cardiac wall motion. Recently, a myocardial motion tracking technique (Wall Motion Tracking) using a pattern matching technique has been commercialized, and used clinically. This technique is, however, dependent on the image quality of ultrasonic images. Using a contrast medium will improve the image quality of a cardiac image. Therefore, a contrast medium may be used in combination with tracking processing.

However, the influence of speckle pattern noise due to a contrast medium will degrade tracking accuracy on the boundary portions between cardiac chambers and cardiac muscle.

BRIEF DESCRIPTION OF THE DRAWINGS

FIG. 2 is a flowchart showing a processing procedure by this embodiment;

FIG. 4 is a view showing an example of a cardiac chamber ROI and myocardial ROI set in step S12 in FIG. 2;

FIG. 5 is a view for a supplementary explanation of steps S15, S17, and S20 in FIG. 2, showing temporal changes in the average signal/echo intensity of a cardiac chamber ROI and myocardial ROI;

FIG. 7 is a view showing the tracking result obtained by the myocardial tracking processing unit in FIG. 1 using a contrast medium.

DETAILED DESCRIPTION

In general, according to one embodiment, an ultrasonic diagnosis apparatus includes a display unit to display an ultrasonic image, a comparison unit to compare the signal/echo intensity of a cardiac chamber portion of an ultrasonic image with the signal/echo intensity of a myocardial portion of the image, and an indication generating unit to generate a specific indication at a time point when the signal/echo intensity of the cardiac chamber portion changes from a higher value to a lower value than the signal/echo intensity of the myocardial portion or at another time point with reference to the time point.

Figure 1:
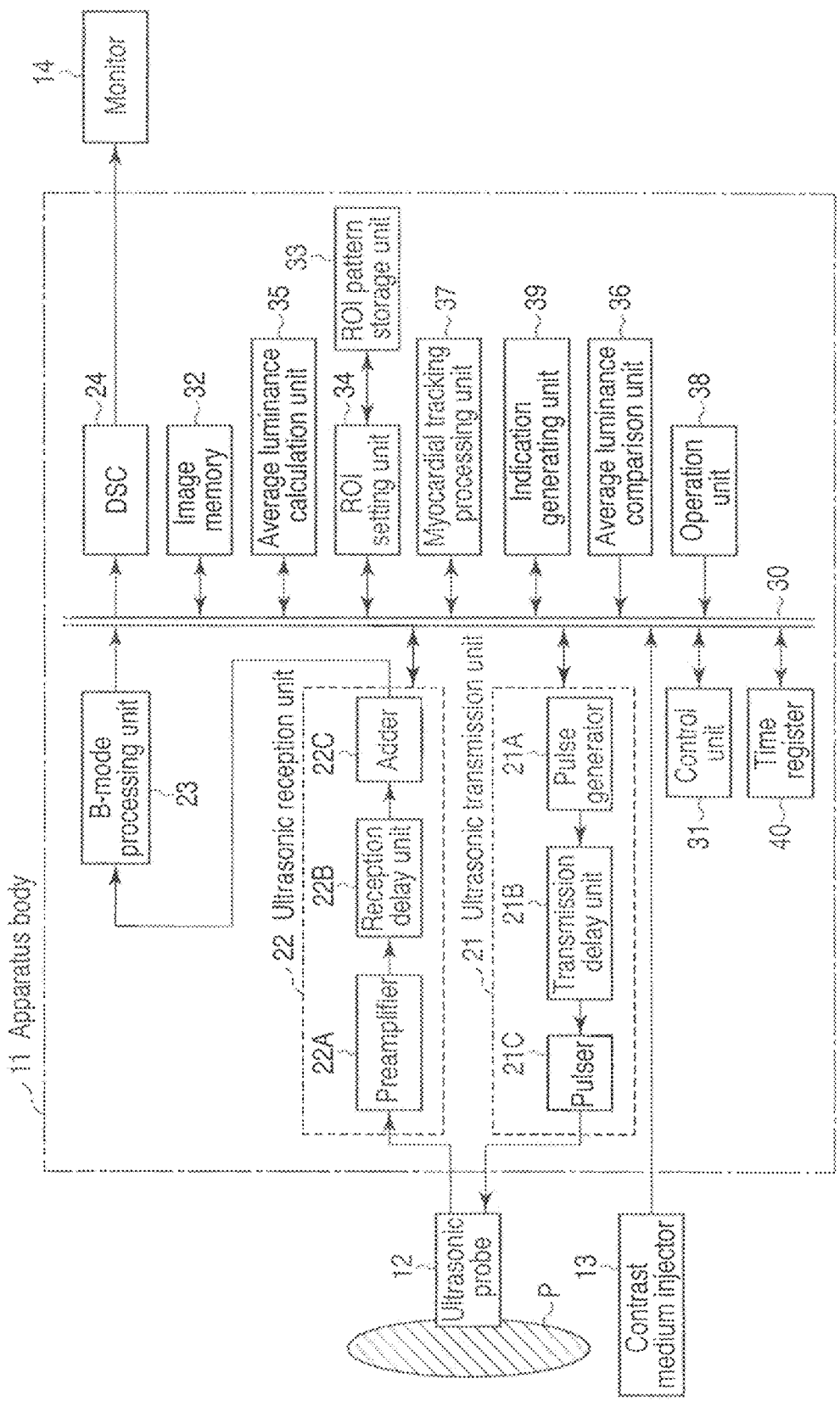
FIG. 1 is a block diagram showing the arrangement of an ultrasonic diagnosis apparatus according to an embodiment.

FIG. 1 is a block diagram showing the arrangement of the ultrasonic diagnosis apparatus according to this embodiment. A multi-channel ultrasonic probe 12 includes a plurality of transducers arranged in an array. Each transducer includes a piezoelectric element, an individual electrode formed on the upper surface of the piezoelectric element, and a common electrode formed on the lower surface of the piezoelectric element. One channel is constituted by one or a plurality of neighboring transducers. An apparatus body 11 housed in a console case is connected to the ultrasonic probe 12.

The apparatus body 11 includes a transmission unit 21 and reception unit 22 connected to the ultrasonic probe 12. The transmission unit 21 is provided with a pulser 21C connected to each transducer. The pulser 21C applies a driving signal (high-frequency voltage signal) to each corresponding transducer in response to a pulse signal, as a trigger, which is generated from a pulse generator 21A at a predetermined period (the reciprocal of a pulse repetition frequency PRF) and delayed by a transmission delay unit 21B.

The ultrasonic waves generated by the mechanical vibrations of transducers based on driving signals propagate in an object, are reflected by a discontinuity surface of acoustic impedance along the propagation path, and return as echoes to the ultrasonic probe 12. The echoes mechanically vibrate piezoelectric elements of the ultrasonic probe 12. A preamplifier 22A of the reception unit 22 amplifies the weak electrical signals generated by the vibrations. A reception delay unit 22B then delays the signals. An adder 22C adds the signals (phasing addition processing). This gives directivity to the echo signal. The echo signal obtained by such addition will be referred to as a reception signal hereinafter.

A B-mode processing unit 23 includes a detection circuit, a logarithmic amplifier, and an analog/digital converter. The detection circuit detects the ultrasonic waves (reception signal) reflected by an acoustic impedance boundary in a living body, and outputs the envelope of the ultrasonic waves. The logarithmic amplifier logarithmically amplifies the output signal from the detection circuit. The analog/digital converter further converts the signal into a digital signal and outputs it as ultrasonic image data.

The output of the B-mode processing unit 23 is connected to a data/control bus 30. A digital scan converter (DSC) 24 is connected to the data/control bus 30. The digital scan converter 24 superimposes graphics such as a pointer and an ROI mark on the ultrasonic image in an ultrasonic scan scheme, rearranges the information in accordance with the video scan scheme of a monitor 14, and outputs the resultant information.

The units connected to the data/control bus 30 include a control unit 31, an image memory 32, an ROI pattern storage unit 33, an ROI setting unit 34, an average luminance calculation unit 35, an average luminance comparison unit 36, a myocardial tracking processing unit 37, an operation unit 38, an indication generating unit 39, and a time register 40. The image memory 32 stores and retains the ultrasonic image data output from the B-mode processing unit 23 in accordance with a control signal for the storage of image data from the control unit 31. When receiving no control signal from the control unit 31, the image memory 32 does not store ultrasonic image data or overwrites the ultrasonic image data but does not retain the data.

The ROI pattern storage unit 33 stores and holds the data of a plurality of ROI patterns and the data of a plurality of sampled ultrasonic images in advance. The data of each ROI pattern defines the sizes and positions of two, typically circular, ROIs respectively corresponding to a cardiac chamber region and a myocardial region on a long-axis cardiac ultrasonic image. A plurality of sampled ultrasonic images are respectively associated with a plurality of ROI patterns. The two ROIs defined by an ROI pattern are set to sizes and positions suitable for a cardiac chamber region and a myocardial region on a sampled ultrasonic image associated with each ROI pattern.

The ROI setting unit 34 sets a cardiac chamber ROI and a myocardial ROI on a live ultrasonic image actually acquired from an object, based on a specific ROI pattern selected from the plurality of ROI patterns stored in the ROI pattern storage unit 33. The ROI setting unit 34 selects a sampled ultrasonic image most similar to a live ultrasonic image, and selects an ROI pattern associated with the selected sampled ultrasonic image as a specific ROI pattern. Typically, the ROI setting unit 34 subtracts the live ultrasonic image and each sampled ultrasonic image from each other, and selects a sampled ultrasonic image exhibiting a minimum sum of squares of the difference.

The average luminance calculation unit 35 calculates, for the live ultrasonic image, the average luminance of the pixels in the set cardiac chamber ROI and the average luminance of the pixels in the set myocardial ROI. The signal intensity or the echo intensity is finally converted into luminance according to the gray scale or color table. Therefore the average luminance can be replaced the average signal /echo intensity.

The average luminance comparison unit 36 compares the calculated average luminance of the cardiac chamber ROI with the calculated average luminance of the myocardial ROI.

The control unit 31 controls the indication generating unit 39, in accordance with the comparison result between the average luminance of the cardiac chamber ROI and the average luminance of the myocardial ROI, to generate a preset indication. The control unit 31 also controls the image memory 32 to store the live ultrasonic image data. Typically, an indication is message data using a text representing, for example, that an image suitable for speckle tracking has been acquired. Typically, a message is presented as the text "image suitable for speckle tracking has been acquired". The monitor 14 displays this message after the digital scan converter 24 superimposes it on the live ultrasonic image. The indication may be presented by changing part of an ultrasonic image, typically the color of a boundary frame between cardiac muscle and a cardiac chamber or in another display form. Assume that such an indication is a message in the following description.

In practice, after the injection of a contrast medium, the average luminance of the cardiac chamber ROI increases and exceeds the average luminance of the myocardial ROI. Thereafter, as the contrast medium flows out from the cardiac chamber with the lapse of time, the average luminance of the cardiac chamber ROI changes to become lower than that of the myocardial ROI. At the time of this change (at the start of this change), a message is displayed, and the image memory 32 starts to store live ultrasonic image data. Note that the message may be displayed and the image memory 32 may start to store the live ultrasonic image data at a time point a predetermined time after the change time point as a reference or an estimated time point a predetermined time before the change time point.

The control unit 31 controls the time register 40 to start measuring an elapsed time at the above change time point. The time register 40 measures an elapsed time from the above change time point. The monitor 14 displays the measured elapsed time.

The control unit 31 also compares the average luminance of the cardiac chamber ROI with a preset threshold. When the average luminance of the cardiac chamber ROI becomes lower than the threshold, the control unit 31 controls the indication generating unit 39 to generate message data and end the storage of live ultrasonic image data. This message is presented as, for example, the text "acquisition of image suitable for speckle tracking is complete".

At the same time, the control unit 31 further controls the ultrasonic transmission unit 21 and the ultrasonic reception unit 22 to end ultrasonic scanning.

Note that the control unit 31 may end ultrasonic scanning at a time point when a predetermined period of time has elapsed since the change time point measured by the time register 40. In accordance with a selection instruction issued by the operator in advance, the control unit 31 selects whether to end ultrasonic scanning at a time point when the average luminance of the cardiac chamber ROI becomes lower than the threshold or at a time point when a predetermined time has elapsed since the change time point measured by the time register 40. When the control unit 31 ends ultrasonic scanning at a time point when a predetermined time has elapsed since the change time point measured by the time register 40, the monitor 14 displays the remaining time before the end of ultrasonic scanning.

Note that the operation unit 38 includes operation buttons in the form of real or icon buttons which are manually operated to issue instructions to start and end storing live ultrasonic image data into the image memory 32. The operator can arbitrarily select in advance whether to manually issue instructions to start and end storing live ultrasonic image data into the image memory 32 or to make the control unit 31 automatically control storing operation as described above.

FIG. 2 shows a processing procedure in this embodiment. First of all, the ultrasonic transmission unit 21 and the ultrasonic reception unit 22 start ultrasonic scanning on a long-axis slice of a cardiac region of an object, as a scan surface, via the ultrasonic probe 12 (S11). Ultrasonic scanning is continuously repeated up to step S21 (to be described later). Concurrently with ultrasonic scanning, the B-mode processing unit 23 instantly generates ultrasonic image data based on a reception signal. This image is displayed as a grayscale image on the monitor 14 via the digital scan converter 24. Although the ultrasonic image data generated by the B-mode processing unit 23 is also supplied to the image memory 32, the data is only overwritten and not stored until a control signal for the start of storage (to be described later) is received from the control unit 31.

The ROI setting unit 34 reads, from the image memory 32, ultrasonic image data corresponding to a specific cardiac phase which is set in advance, under the control of the control unit 31. The ROI setting unit 34 subtracts the ultrasonic image from each of the plurality of sampled ultrasonic images stored in the ROI pattern storage unit 33, and calculates the sums of squares of the differences. The ROI setting unit 34 selects a sampled ultrasonic image exhibiting a minimum of the calculated sums of squares, and reads out the data of an ROI pattern associated with the selected sampled ultrasonic image from the ROI pattern storage unit 33. With this operation, the ROI setting unit 34 sets a cardiac chamber ROI and a myocardial ROI (S12). The ROI setting unit 34 supplies the data of the ROI pattern to the average luminance calculation unit 35.

Subsequently, a contrast medium is injected from a contrast medium injector 13 into an object at a proper timing. As a consequence, the contrast medium injector 13 outputs a signal representing the start of the administration of a contrast medium to the control unit 31 (S13). In response to this signal as a trigger, the average luminance calculation unit 35 sequentially receives ultrasonic image data sequentially generated by ultrasonic scanning, via the image memory 32, under the control the control unit 31. The average luminance calculation unit 35 repeatedly calculates an average luminance AVv of the pixels in the cardiac chamber ROI and an average luminance AVm of the pixels in the myocardial ROI, which are based on the ROI pattern exemplified in FIG. 4 (S14).

Figure 3:
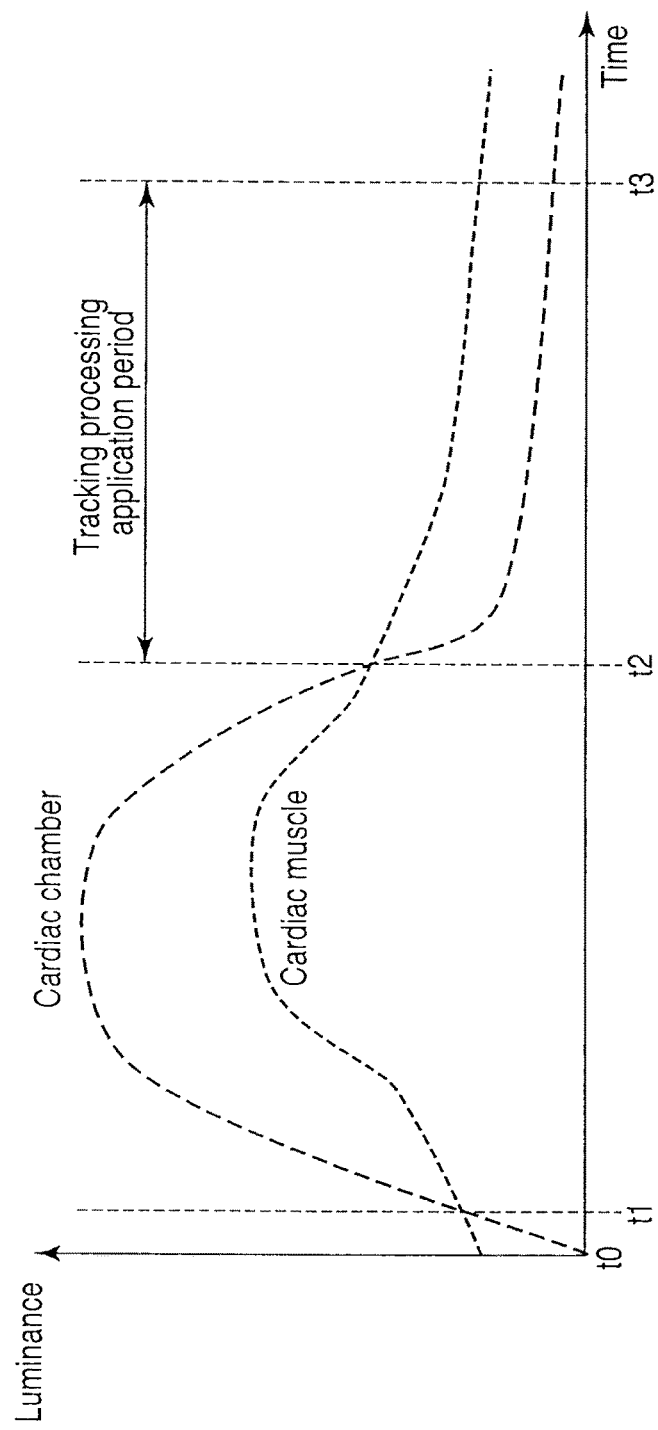
FIG. 3 is a graph showing an example of an image before the injection of a contrast medium in FIG. 2.

FIG. 3 shows temporal changes in the average luminance AVv of the pixels in the cardiac chamber ROI and the average luminance AVm of the pixels in the myocardial ROI. Referring to FIG. 3, time t0 is the time when a contrast medium is administered. In a period before the contrast medium flows into the cardiac chamber, the average luminance AVv of the pixels in the cardiac chamber ROI is lower than the average luminance AVm of the pixels in the myocardial ROI.

The average luminance comparison unit 36 compares the average luminance AVv of the cardiac chamber ROI with the average luminance AVm of the myocardial ROI, which are calculated by the average luminance calculation unit 35. First, the average luminance comparison unit 36 determines whether the average luminance AVv of the cardiac chamber ROI is higher than the average luminance AVm of the myocardial ROI (S15). The change point at which the average luminance AVv of the cardiac chamber ROI becomes higher than the average luminance AVm of the myocardial ROI indicates that the contrast medium has flowed into the cardiac chamber. This change point corresponds to time t1. The average luminance calculation unit 35 continuously and repeatedly calculates the average luminance AVv of the pixels in the cardiac chamber ROI and the average luminance AVm of the pixels in the myocardial ROI (S16).

The average luminance comparison unit 36 again compares the average luminance AVv of the cardiac chamber ROI with the average luminance AVm of the myocardial ROI, which are calculated by the average luminance calculation unit 35. This time, the average luminance comparison unit 36 determines whether the average luminance AVv of the cardiac chamber ROI is lower than the average luminance AVm of the myocardial ROI (S17). The time point at which the average luminance AVv of the cardiac chamber ROI changes from a higher value to a lower value than the average luminance AVm of the myocardial ROI indicates that the contrast medium gradually flows out from the cardiac chamber to stabilize the contrast medium density in the cardiac chamber at a proper density in speckle tracking processing including the processing of identifying the interface of the cardiac muscle relative to the cardiac chamber. This time point corresponds to time t2.

At time t2 when the average luminance AVv of the cardiac chamber ROI has changed from a higher value to a lower value than the average luminance AVm of the myocardial ROI, the indication generating unit 39 generates message data under the control of the control unit 31. The digital scan converter 24 superimposes the message data on a live ultrasonic image. The monitor 14 then displays the resultant image, as exemplified by FIG. 5 (S18). For example, the message "image suitable for speckle tracking has been acquired" is displayed on the screen of the image display 18 upon being superimposed on a live ultrasonic image (S18). At the same time, the image memory 32 starts to store live ultrasonic image data under the control of the control unit 31 (S19). The image memory 32 continuously stores live ultrasonic image data until the control unit 31 determines the end of the processing in step S21.

Note that when seeing the message, the operator may start storing live ultrasonic image data by issuing an instruction to start the storage of live ultrasonic image data by operating the operation unit 38.

The average luminance comparison unit 36 compares the average luminance AVv of the cardiac chamber ROI calculated by the average luminance calculation unit 35 with the preset threshold (S20). A change in the average luminance AVv of the cardiac chamber ROI to a value lower than the threshold represents that the effect of the contrast medium in the cardiac chamber has become unsuitable for speckle tracking processing. This time point corresponds to time t3.

At time t3 when the average luminance AVv of the cardiac chamber ROI has changed to a value lower than the threshold, the monitor 14 stops displaying the message on the screen under the control of the control unit 31. At the same time, the control unit 31 stops ultrasonic scanning and stops storing live ultrasonic image data in the image memory 32 (S21).

Note that it is possible to stop storing live ultrasonic image data by making the operator operate the operation unit 38 to issue an instruction to end the storage of live ultrasonic image data upon seeing that the message is turned off.

Figure 6:
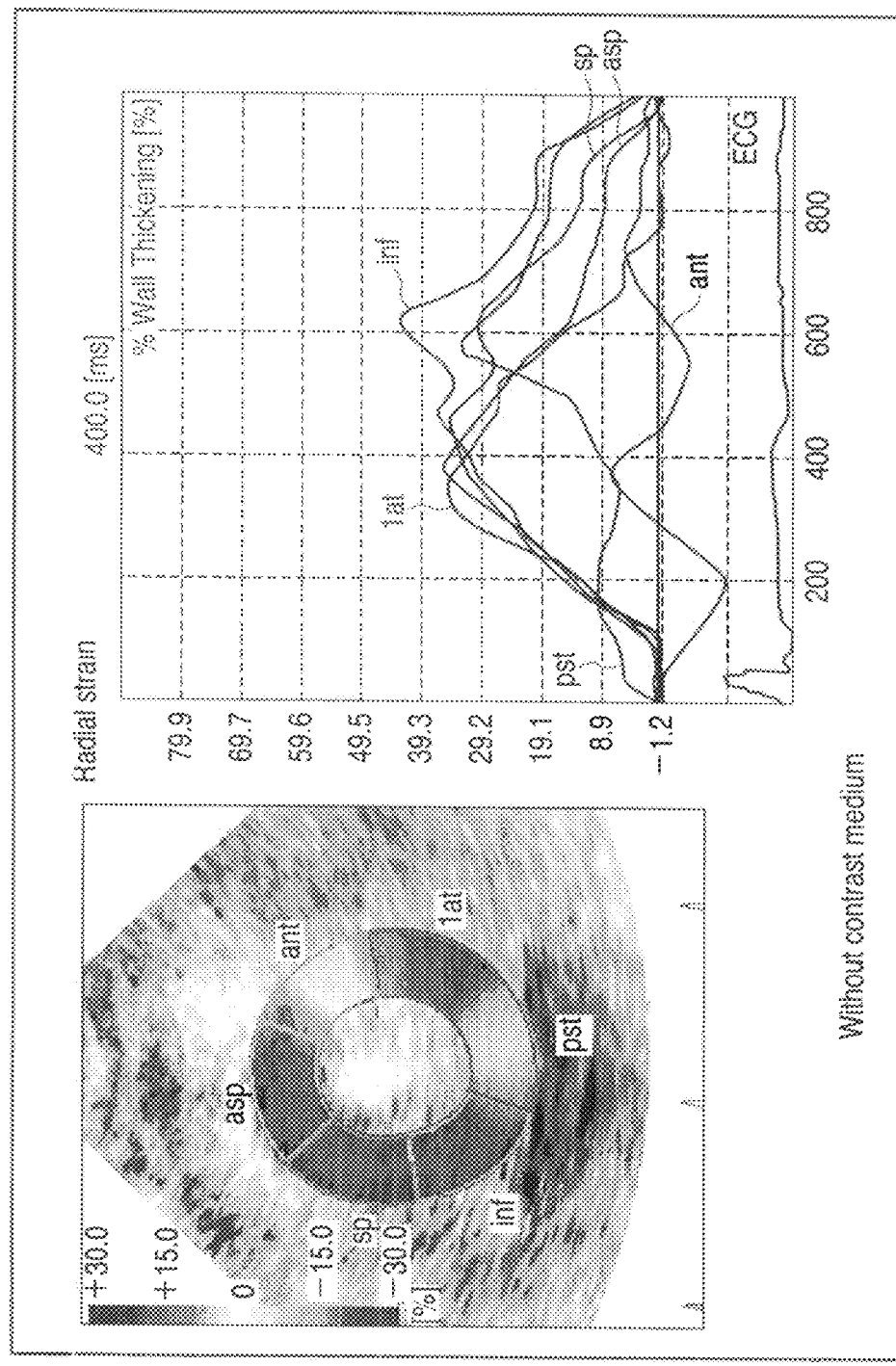
FIG. 6 is a view showing the tracking result obtained by a myocardial tracking processing unit in FIG. 1 without using any contrast medium.

As described above, ultrasonic image data is stored in the period between time t2 when the average luminance AVv of the cardiac chamber ROI has changed from a higher value to a lower value than the average luminance AVm of the myocardial ROI and time t3 when the average luminance AVv of the cardiac chamber ROI has changed to a value lower than the threshold. The myocardial tracking processing unit 37 executes myocardial tracking processing by using a plurality of ultrasonic image data stored in this period. FIGS. 6 and 7 each show a result example display based on a myocardial tracking processing result. Myocardial regions are extracted from a plurality of ultrasonic images. The extracted myocardial regions each are segmented into a plurality of segments. The radial expansion/contraction ratio of each myocardial segment on a reference image relative to the center of the cardiac chamber is calculated. A segment mark is then superimposed and displayed on an ultrasonic image with a hue corresponding to the expansion/contraction ratio. Temporal changes in the radial expansion/contract ratio of each segment are displayed in the form of a graph.

This embodiment can calculate an accurate speckle tracking processing result by improving degradation in the tracking accuracy of a boundary portion between the cardiac chamber and the cardiac muscle due to the influence of speckle pattern noise caused by a contrast medium and executing speckle tracking processing using an ultrasonic image with suitable image quality.

According to the above description, the image memory 32 stores a plurality of ultrasonic image data generated in the period between start time point t2 and end time point t3, and myocardial tracking processing is executed for the stored ultrasonic image data. However, it is possible to store, in the image memory 32 in advance, all ultrasonic image data generated after time t0 at which scanning starts or time t1 and execute myocardial tracking processing for a plurality of ultrasonic image data generated in the period between start time t2 and end time t3, which are extracted from the stored ultrasonic image data.

While certain embodiments have been described, there embodiments have been presented by way of example only, and are not intended to limited the scope of the inventions. Indeed, the novel methods and systems described herein may be embodied in a variety of other forms; furthermore, various omissions, substitutions and changes in the form of the methods and systems described herein may be made without departing form the spirit of the inventions. The accompanying claims and their equivalents are intended to cover such forms or modifications as would fall within the scope and spirit of the inventions.

What is claimed is:

1. An ultrasonic diagnosis apparatus which generates, during a scanning process, a plurality of ultrasonic images by repeatedly scanning an interior of an object after injection of a contrast medium by using an ultrasonic wave, the apparatus comprising:
   a display unit configured to display the ultrasonic images; and
   processing circuitry configured to
      compare, repeatedly during the scanning process, a signal or echo intensity of a cardiac chamber portion of an ultrasonic image with a signal or echo intensity of a myocardial portion of the ultrasonic image each time the signal or echo intensity of the cardiac chamber portion and the signal or echo intensity of the myocardial portion are obtained;
      detect, during the scanning process, a time point at which the signal or echo intensity of the cardiac chamber portion changes from being higher than the signal or echo intensity of the myocardial portion to being lower than the signal or echo intensity of the myocardial portion;
      track a contour of a specific region in the ultrasonic images, the tracking of the contour of the specific region being with respect to one of the ultrasonic images generated after the time point; and
      cause the display to display, during the scanning process, a specific indication in response to detection of the time point.

2. The apparatus according to claim 1, wherein the processing circuitry is further configured to compare an average signal or echo intensity of a cardiac chamber region of interest (ROI) of each ultrasonic image with an average signal or echo intensity of a myocardial ROI of each ultrasonic image.

3. The apparatus according to claim 2, wherein the processing circuitry is further configured to set positions and sizes of the cardiac chamber ROI and the myocardial ROI in accordance with a specific ROI pattern selected from a plurality of ROI patterns.

4. The apparatus according to claim 3, wherein the processing circuitry is further configured to select the specific ROI pattern based on a correlation between one of the ultrasonic images and a plurality of sampled ultrasonic images respectively corresponding to the plurality of ROI patterns.

5. The apparatus according to claim 3, wherein the processing circuitry is further configured to change the positions and sizes of the cardiac chamber ROI and myocardial ROI in accordance with a cardiac phase.

6. The apparatus according to claim 1, wherein the processing circuitry is further configured to generate indication data indicating that an image suitable for speckle tracking is acquired.

7. The apparatus according to claim 1, wherein the processing circuitry is further configured to generate data for causing the display to display a message indicating that an image suitable for speckle tracking is acquired.

8. The apparatus according to claim 1, wherein the processing circuitry is further configured to generate data for changing a color of a portion of each displayed ultrasonic image.

9. The apparatus according to claim 1, further comprising an image memory,
   wherein the processing circuitry is further configured to control the image memory to store at least one of the ultrasonic images generated after the time point.

10. The apparatus according to claim 1, further comprising an image memory,
    wherein the processing circuitry is further configured to control the image memory to store at least one of the ultrasonic images generated in a period between the time point and a time point occurring a predetermined time after the time point.

11. The apparatus according to claim 1, wherein the processing circuitry is further configured to track the contour of the specific region with respect to one of the ultrasonic images generated in a period between the time point and a time point occurring a predetermined time from the time point.

12. The apparatus according to claim 1, wherein the display is further configured to display an elapsed time from the time point.

13. The apparatus according to claim 1, wherein the processing circuitry is further configured to stop the scanning process at a time point occurring a predetermined time from the time point.

14. The apparatus according to claim 1, wherein the processing circuitry is further configured to measure an elapsed time from the time point.

15. The apparatus according to claim 14, wherein the display is further configured to display the measured elapsed time.

16. A method for displaying a plurality of ultrasonic images generated, during a scanning process, by repeatedly scanning an interior of an object after injection of a contrast medium, the method comprising:
    injecting a contrast medium into the object;
    generating the plurality of ultrasonic images;
    comparing, repeatedly during the scanning process, a signal or echo intensity of a cardiac chamber portion of the ultrasonic image with a signal or echo intensity of a myocardial portion of the ultrasonic image each time the signal or echo intensity of the cardiac chamber portion and the signal or echo intensity of the myocardial portion are obtained; and
    detecting, during the scanning process, a time point at which the signal or echo intensity of the cardiac chamber portion changes from being higher than the signal or echo intensity of the myocardial portion to being lower than the signal or echo intensity of the myocardial portion;
    tracking a contour of a specific region in the ultrasonic images, the tracking of the contour of the specific region being with respect to one of the ultrasonic images generated after the time point; and
    displaying, during the scanning process, a specific indication in response to the detecting of the time point.

17. The method according to claim 16, wherein the indication indicates that an ultrasonic image suitable for speckle tracking is acquired.

18. The method according to claim 16, wherein the indication is represented by changing a color of a portion of the displayed ultrasonic image.

19. An ultrasonic diagnosis apparatus which generates, during a scanning process, a plurality of ultrasonic images by repeatedly scanning an interior of an object after injection of a contrast medium by using an ultrasonic wave, the apparatus comprising:
- a display configured to display the ultrasonic images; and
- processing circuitry configured to
  - compare, repeatedly during the scanning process, a signal or echo intensity of a cardiac chamber portion of an ultrasonic image with a signal or echo intensity of a myocardial portion of the ultrasonic image each time the signal or echo intensity of the cardiac chamber portion and the signal or echo intensity of the myocardial portion are obtained; and
  - detect, during the scanning process, a time point at which the signal or echo intensity of the cardiac chamber portion changes from being higher than the signal or echo intensity of the myocardial portion to being lower than the signal or echo intensity of the myocardial portion:
  - track a contour of a specific region in the ultrasonic images, the tracking of the contour of the specific region being with respect to one of the ultrasonic images generated after the time point; and
  - cause the display to display, during the scanning process, a specific indication at a timing when a time point at which the signal or echo intensity of the cardiac chamber portion changes from being higher than the signal or echo intensity of the myocardial portion to being lower than the signal or echo intensity of the myocardial portion,
- wherein the indication is represented by changing a color of a portion of one of the displayed ultrasonic images.

* * * * *